US012686694B2

(12) United States Patent
Haas et al.

(10) Patent No.: US 12,686,694 B2
(45) Date of Patent: *Jul. 21, 2026

(54) METHOD OF EXTRACTING CARBONIC ACID, ALIPHATIC ACIDS, ESTERS AND ALCOHOLS FROM AN AQUEOUS MEDIUM

(71) Applicant: EVONIK OPERATIONS GMBH, Essen (DE)

(72) Inventors: Thomas Haas, Münster (DE); Christian Richter, Münster (DE)

(73) Assignee: Evonik Operations GmbH, Essen (DE)

( * ) Notice: Subject to any disclaimer, the term of this patent is extended or adjusted under 35 U.S.C. 154(b) by 857 days.

This patent is subject to a terminal disclaimer.

(21) Appl. No.: 17/630,353

(22) PCT Filed: Jul. 23, 2020

(86) PCT No.: PCT/EP2020/070767

§ 371 (c)(1),
(2) Date: Jan. 26, 2022

(87) PCT Pub. No.: WO2021/018717

PCT Pub. Date: Feb. 4, 2021

(65) Prior Publication Data

US 2022/0289773 A1 Sep. 15, 2022

(30) Foreign Application Priority Data

Jul. 29, 2019 (EP) .................................... 19188880

(51) Int. Cl.

| | |
|---|---|
| ***C07C 29/86*** | (2006.01) |
| ***B01D 11/04*** | (2006.01) |
| ***C07C 51/48*** | (2006.01) |
| ***C07F 9/53*** | (2006.01) |

(52) U.S. Cl.

CPC ........ *C07F 9/5304* (2013.01); *B01D 11/0492* (2013.01); *C07C 29/86* (2013.01); *C07C 51/48* (2013.01)

(58) Field of Classification Search

CPC ... C07F 9/5304; B01D 11/0492; C07C 29/86; C07C 51/48

See application file for complete search history.

(56) References Cited

U.S. PATENT DOCUMENTS

| | | | |
|---|---|---|---|
| 4,153,809 | A | 5/1979 | Suzuki |
| 4,544,779 | A | 10/1985 | Bright |
| 4,705,894 | A | 11/1987 | Su et al. |
| 4,714,791 | A | 12/1987 | Inada et al. |
| 5,175,357 | A | 12/1992 | Van Brunt |
| 7,122,709 | B2 | 10/2006 | Fanselow et al. |
| 8,703,843 | B2 | 4/2014 | Atkinson et al. |
| 10,053,411 | B2 | 8/2018 | Dishisha et al. |
| 10,144,904 | B2 | 12/2018 | Wiesmueller et al. |
| 11,124,813 | B2 | 9/2021 | Haas et al. |
| 11,174,496 | B2 | 11/2021 | Haas et al. |
| 2003/0012715 | A1 | 1/2003 | Bond et al. |
| 2006/0096849 | A1 | 5/2006 | Kerker et al. |
| 2007/0275447 | A1 | 11/2007 | Lewis et al. |
| 2008/0057554 | A1 | 3/2008 | Huhnke et al. |
| 2008/0119668 | A1 | 5/2008 | Nordhoff et al. |
| 2010/0210871 | A1 | 8/2010 | Kobler et al. |
| 2013/0164797 | A1 | 6/2013 | Gielen et al. |
| 2014/0106421 | A1 | 4/2014 | Yin et al. |
| 2014/0303408 | A1 | 10/2014 | Zaher |
| 2016/0215302 | A1 | 7/2016 | Haas et al. |
| 2017/0183696 | A1 | 6/2017 | Nouaille et al. |
| 2019/0169654 | A1 | 6/2019 | Hecker et al. |

(Continued)

FOREIGN PATENT DOCUMENTS

| | | | | |
|---|---|---|---|---|
| CN | 102875384 A | * | 1/2013 | ........... C07C 201/16 |
| DE | 3626968 | | 2/1988 | |

(Continued)

OTHER PUBLICATIONS

CN 102875384 A (Yang et al.; English language machine translation).*

(Continued)

*Primary Examiner* — Amy C Bonaparte
*Assistant Examiner* — Derek Rhoades
(74) *Attorney, Agent, or Firm* — Law Office of: Michael A. Sanzo, LLC

(57) ABSTRACT

The present invention relates to a method of extracting at least one selected from carbonic acid, aliphatic acid, aliphatic acid ester and aliphatic alcohol from an aqueous medium, the method comprising the steps:

(a) contacting the carbonic acid, aliphatic acid, aliphatic acid ester and/or aliphatic alcohol in the aqueous medium with an extracting medium containing at least one alkyl-phosphine oxide for a time sufficient to extract the carbonic acid, aliphatic acid, aliphatic acid ester and/or aliphatic alcohol from the aqueous medium into the extracting medium, and (b) separating the extracting medium with the extracted carbonic acid, aliphatic acid, aliphatic acid ester and/or aliphatic alcohol from the aqueous medium, characterized in, that the at least one alkyl-phosphine oxide contains at least two different alkyl radicals per alkyl-phosphine oxide molecule and the aqueous medium in (a) contains a microorganism, preferably a living microorganism, producing the carbonic acid, aliphatic acid, aliphatic acid ester and/or aliphatic alcohol.

19 Claims, No Drawings

(56) References Cited

U.S. PATENT DOCUMENTS

| | | | |
|---|---|---|---|
| 2020/0377914 | A1 | 12/2020 | Haas et al. |
| 2022/0281789 | A1 | 9/2022 | Haas et al. |

FOREIGN PATENT DOCUMENTS

| | | |
|---|---|---|
| EP | 0 157 183 | 10/1985 |
| EP | 0 732 320 | 9/1995 |
| GB | 2191490 | 12/1987 |
| JP | S53121713 | 10/1978 |
| JP | 2007082490 | 4/2007 |
| RU | 2038840 | 7/1995 |
| WO | WO 84/04923 | 12/1984 |
| WO | WO 85/00805 | 2/1985 |
| WO | WO 98/00558 | 1/1998 |
| WO | WO 99/38834 | 8/1999 |
| WO | WO 00/68407 | 11/2000 |
| WO | WO 2009/059228 | 5/2009 |
| WO | WO 2019/002240 | 1/2019 |
| WO | WO 2020/104411 | 5/2020 |

OTHER PUBLICATIONS

Watson, et al., "A Liquid Phosphine Oxide: Solvent Extraction of Phenol, Acetic Acid and Ethanol," *Solvent Extraction and Ion Exchange* 6(2):207-220 (1988).

International Search Report for corresponding PCT/EP2020/070767, filed Jul. 23, 2020.

Written Opinion of the International Searching Authority for corresponding PCT/EP2020/070767, filed Jul. 23, 2020.

International Preliminary Report on Patentability for corresponding PCT/EP2020/070767, filed Jul. 23, 2020.

European Search Report and Search Opinion for EP 19188880.9, filed Jul. 29, 2019, corresponding to PCT/EP2020/070767.

International Search Report for international application PCT/EP2020/070765, filed Jul. 23, 2020, corresponding to copending U.S. Appl. No. 17/630,435.

Written Opinion of the International Searching Authority for international application PCT/EP2020/070765, filed Jul. 23, 2020, corresponding to copending U.S. Appl. No. 17/630,435.

International Preliminary Report on Patentability for international application PCT/EP2020/070765, filed Jul. 23, 2020, corresponding to copending U.S. Appl. No. 17/630,435.

European Search Report and Search Opinion for EP 19188881.7 filed Jul. 29, 2019, corresponding to PCT/EP2020/070765.

Database XP-002796868 cited in the International Search Report for international application PCT/EP2020/070765 to accompany JP S53121713.

Gildemyn, et al., "Upgrading syngas fermentation effluent using *Clostridium kluyveri* in a continuous fermentation," *Biotechnol Biofuels* 10:83 pp. 1-15 (Mar. 2017).

Jeon, et al., "Production of medium-chain carboxylic acids by *Megasphaera* sp. MH with supplemental electron acceptors," *Biotechnol Biofuels* 9:129, pp. 1-9 (Jun. 2016).

Morinaga, et al., "The production of acetic acid from carbon dioxide and hydrogen by an anaerobic bacterium," *Journal of Biotechnology* 14(2):187-194 (May 1990).

Naveira, et al., "H-B-E (hexanol-butanol-ehtanol) fermentation for the production of higher alcohols from syngas/waste gas," *Journal of Chemical Technology & Biotechnology* 92(4): (Apr. 2017).

Sakai, et al., "Ethanol production from $H_2$ and $CO_2$ by a newly isolated thermophilic bacterium, *Moorella* sp. HUC22-1," *Biotechnology Letters* 26(20):1607-1612 (Oct. 2004).

Schmidt, et al., "Production of Acetic Acid from Hydrogen and Carbon Dioxide by *Clostridium* Species ATCC 29797," *Chem Eng Commun* 45(1-6):61-73 (May 1986).

Weiben, et al., "Extraction Equilibria of Formic and Acetic Acids from Aqueous Solution by Phosphate-Containing Extractants," *J. Chem. Eng. Data* 46(6):1472-1475 (Nov. 2001).

U.S. Appl. No. 17/630,435, filed Jan. 26, 2022, Haas.

De Poures, et al., "1-Hexanol as a sustainable biofuel in DI diesel and its effect on combustion and emissions under the influence of injection timing and exhaust gas recirculation (EGR)," *Applied Thermal Engineering* 113:1505-1513 (2017).

Phillips, et al., "Butanol and hexanol production in *Clostridium carboxidivorans* syngas fermentation: Medium development and culture techniques," *Bioresource Technology* 190:114-121 (2015).

Richter, et al., "A Narrow pH Supports Butanol, Hexanol and Octanol Production from Syngas in a Continuous Co-culture of *Clostridium ijungdahlii* and *Clostridium kluyveri* with In-Line Product Extraction," *Frontiers in Microbiology* 7: Article 1773 (2016).

Non Final Office Action for copending U.S. Appl. No. 17/630,435 mailed Sep. 4, 2024.

U.S. Appl. No. 16/969,853, filed Feb. 15, 2019, US-2020/0377914 A1, Dec. 3, 2020, Haas.

Amendment & Response to Non Final Office Action filed Mar. 5, 2025 for copending U.S. Appl. No. 17/630,435.

Amendment & Response to Non Final Office Action filed Dec. 1, 2024 for copending U.S. Appl. No. 17/630,435.

Non Final Office Action for copending U.S. Appl. No. 17/630,435, mailed Dec. 6, 2024.

Final Office Action mailed May 28, 2025 for copending U.S. Appl. No. 17/630,435.

Martak, et al., "Toxicity of Organic Solvents Used In Situ in Microbial Fermentation," Biotechnology Techniques 9 (4):247-252 (Apr. 1995).

Nuchnio, et al., "Extractive Acidogenic Fermentation by a Supported Liquid Membrane," Ferment. Technol. 65 (6):699-702 (1987).

Von Frieling, et al., "Recovery of lactic acid from aqueous model solutions and fermentation broths," Process Biochemistry 34:685-696 (1999).

Amendment & Response to Final Office Action filed Aug. 24, 2025 for copending U.S. Appl. No. 17/630,435.

RCE to Accompany Amendment & Response to Final Office Action filed Aug. 24, 2025 for copending U.S. Appl. No. 17/630,435.

Notice of Allowance mailed Sep. 16, 2025 for copending U.S. Appl. No. 17/630,435.

* cited by examiner

METHOD OF EXTRACTING CARBONIC ACID, ALIPHATIC ACIDS, ESTERS AND ALCOHOLS FROM AN AQUEOUS MEDIUM

CROSS REFERENCE TO RELATED APPLICATIONS

The present application is US national stage of international application PCT/EP2020/070767, which had an international filing date of Jul. 23, 2020 and which was published on Feb. 4, 2021. The PCT application claims priority to EP 19188880.9, filed on Jul. 29, 2019. The content of these prior filings is hereby incorporated by reference in its entirety.

FIELD OF THE INVENTION

The present invention relates to a method of extracting at least one selected from carbonic acid, aliphatic acid, aliphatic acid ester and aliphatic alcohol from an aqueous medium, the method comprising the steps:

(a) contacting the carbonic acid, aliphatic acid, aliphatic acid ester and/or aliphatic alcohol in the aqueous medium with an extracting medium containing at least one alkyl-phosphine oxide for a time sufficient to extract the alkanoic acid from the aqueous medium into the extracting medium, and (b) separating the extracting medium with the extracted carbonic acid, aliphatic acid, aliphatic acid ester and/or aliphatic alcohol from the aqueous medium, characterized in, that the at least one alkyl-phosphine oxide contains at least two different alkyl radicals per alkyl-phosphine oxide molecule.

BACKGROUND OF THE INVENTION

WO2009059228 discloses a process for recovering acetic acid from a wood extract comprising: providing an aqueous wood extract containing acetic acid and dissolved hemicellulose containing uronic acid; providing a water insoluble solvent containing an extractant for the acetic acid; contacting the wood extract with the solvent and extractant in order to extract the acetic acid from the wood extract; and recovering the acetic acid from the solvent and extractant, wherein the extractant for acetic acid may comprise trioctylphosphine oxide.

U.S. Pat. No. 4,705,894 discloses a process for the recovery of a carboxylic acid selected from the group consisting of citric acid, malic acid, tartaric acid and oxalic acid from fermentation broths with an extractant being a mixture of trialkyl phosphine oxides having a total of 15 to 27 carbon atoms.

There still is a need in the art for a more efficient extraction method of extracting aliphatic acids, esters and alcohols, especially aliphatic acids, produced in industrial scale. Further, there is a need for an extraction method of aliphatic acids, esters and alcohols, especially aliphatic acids, that can be used in connection with a biotechnological method of producing the aliphatic acids, esters and alcohols.

DESCRIPTION OF THE INVENTION

The present invention attempts to solve the problems above by providing a means of extracting aliphatic acids, esters and alcohols, especially aliphatic acids, that is more efficient than the current methods available in the art. The present invention also provides a means of extracting aliphatic acids, esters and alcohols, especially aliphatic acids, that can be used in conjunction with a biotechnological method of producing aliphatic acids, esters and alcohols, especially aliphatic acids.

According to one aspect of the present invention, there is provided a method of extracting at least one selected from carbonic acid, aliphatic acid, aliphatic acid ester and aliphatic alcohol from an aqueous medium as described in claim 1.

Another aspect of the instant invention is an alkyl-phosphine oxide of general formula 1 general formula 1

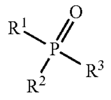

with $R^1$, $R^2$ and $R^3$ selected from alkyl radicals containing 6 to 12, preferably 8 to 10, more preferably 8 or 10, carbon atoms, with the proviso, that at least two of $R^1$, $R^2$ and $R^3$ differ from each other Another aspect of the instant invention is the use of at least one alkyl-phosphine oxide, that contains at least two different alkyl radicals per alkyl-phosphine oxide molecule, for extracting at least one selected from carbonic acid, aliphatic acid, aliphatic acid ester and aliphatic alcohol, especially aliphatic acid, from an aqueous medium, wherein the aqueous medium contains a microorganism, preferably a living microorganism, producing the carbonic acid, aliphatic acid, aliphatic acid ester and/or aliphatic alcohol.

It is an advantage of the instant invention, that the extraction method according to any aspect of the present invention allows for an increase in yield relative to the amount of extractants used. Therefore, with a small volume of extracting medium, a larger yield of liphatic acid, aliphatic acid ester and aliphatic alcohol, especially aliphatic acid, may be extracted.

A further advantage of the instant invention is, that the process can be run at low temperatures without the danger of blockages of the means the process is carried out in.

A further advantage of the instant invention is, that the process can be run without the need of an additional extractant, like for example alkanes.

Yet another advantage of the instant invention is, that the extractant can be easily separated by distillation from the carbonic acid, aliphatic acid, aliphatic acid ester and aliphatic alcohol due to its high boiling point.

A further advantage of the instant invention is, that the extractant is nontoxic to microorganisms. Yet another advantage of the instant invention is, that the extractant can be used in a broad pH-range.

Instantly claimed is a method of extracting at least one selected from carbonic acid, aliphatic acid, aliphatic acid ester and aliphatic alcohol from an aqueous medium, the method comprising the steps:

(a) contacting the carbonic acid, aliphatic acid, aliphatic acid ester and/or aliphatic alcohol in the aqueous medium with an extracting medium containing at least one alkyl-phosphine oxide for a time sufficient to extract the carbonic acid, aliphatic acid, aliphatic acid ester and/or aliphatic alcohol from the aqueous medium into the extracting medium, and (b) separating the extracting medium with the extracted carbonic acid, aliphatic acid, aliphatic acid ester and/or aliphatic alcohol from the aqueous medium, characterized in, that the at least one alkyl-phosphine oxide contains at least two different alkyl radicals per alkyl-phosphine oxide molecule.

Preferably the method of the instant invention comprises the step (c) isolating the extracted carbonic acid, aliphatic acid, aliphatic acid ester and/or aliphatic alcohol from the extracting medium.

As the extracting medium is not harmful to microorganisms, the extracting medium according to any aspect of the present invention may be present when the carbonic acid, aliphatic acid, aliphatic acid ester and/or aliphatic alcohol is biotechnologically produced according to any aspect of the present invention. Therefore, the aqueous medium according to any aspect of the present invention, particularly after step (c) of separating the extracted carbonic acid, aliphatic acid, aliphatic acid ester and/or aliphatic alcohol from the extracting medium, may be recycled back into step (a). This step of recycling allows for the microorganisms to be recycled and reused as the extracting medium according to any aspect of the present invention is not toxic to the microorganisms. This step of recycling the aqueous medium in the method according to any aspect of the present invention has the further advantage of enabling the residue of the carbonic acid, aliphatic acid, aliphatic acid ester and/or aliphatic alcohol from the extracting medium, which was not at first instance extracted from steps (a) and (b) in the first cycle, to be given a chance to be extracted a further time or as many times as the aqueous medium is recycled.

Preferably the method according to the instant invention is characterized in, that the aliphatic acid, is selected from monofunctional aliphatic acids and that in the aliphatic acid ester the aliphatic acid radical is selected from monofunctional aliphatic acid radicals and that the aliphatic alcohol is selected from monohydric alcohols.

Preferably the method according to the instant invention is characterized in, that the aliphatic acid, is selected from monofunctional alkanoic acids and that in the aliphatic acid ester the aliphatic acid radical is selected from monofunctional alkanoic acid radicals and that the aliphatic alcohol is selected from monohydric alkanoic alcohols, wherein preferably the alkanoic chains are unbranched.

Preferably the method according to the instant invention is characterized in, that the aliphatic acid, aliphatic acid ester and/or aliphatic alcohol contains 4 to 18, preferably 4 to 12, even more preferably 6 to 8 carbon atoms, even more preferred the aliphatic acid, aliphatic acid ester and/or aliphatic alcohol is selected from the group butanol, pentanol, hexanol, butanoic acid, pentanoic acid, hexanoic acid and the methyl- and ethyl-esters of these three acids.

The weight ratio of the extracting medium used to the amount of the carbonic acid, aliphatic acid, aliphatic acid ester and/or aliphatic alcohol to be extracted may vary depending on how quick the extraction is to be carried out. The weight ratio preferably varies from 0.5:1 to 1:200, preferably from 1:1 to 100, most preferably from 1:5 to 1 to 15. In one example, the amount of extracting medium is equal to the amount of aqueous medium comprising the carbonic acid, aliphatic acid, aliphatic acid ester and/or aliphatic alcohol. After the step of contacting the extracting medium with the aqueous medium, the two phases (aqueous and organic) are separated using any means known in the art. In one example, the two phases may be separated using a separation funnel. The two phases may also be separated using mixer-settlers, pulsed columns, and the like. In one example the separation of the extracting medium from the carbonic acid, aliphatic acid, aliphatic acid ester and/or aliphatic alcohol may be carried out using distillation, especially in the case that the carbonic acid, aliphatic acid, aliphatic acid ester and/or aliphatic alcohol distills at a significantly lower boiling point than the extracting medium. A skilled person may be able to select the best method of separating the extraction medium from the desired the carbonic acid, aliphatic acid, aliphatic acid ester and/or aliphatic alcohol depending on the characteristics of the carbonic acid, aliphatic acid, aliphatic acid ester and/or aliphatic alcohol desired to be extracted.

Preferably the method according to the instant invention is characterized in, that the alkyl-phosphine oxide is selected from an alkyl-phosphine oxide of general formula 1 general formula 1

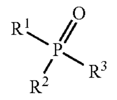

with $R^1$, $R^2$ and $R^3$ selected from alkyl radicals, preferably linear alkyl radicals, containing 4 to 18, preferably 6 to 12, carbon atoms, with the proviso, that at least two of $R^1$, $R^2$ and $R^3$ differ from each other.

Preferably the method according to the instant invention is characterized in, that the alkyl-phosphine oxide is selected from an alkyl-phosphine oxide of general formula 1 with $R^1$, $R^2$ and $R^3$ selected from alkyl radicals, preferably linear alkyl radicals, containing 8 to 10, preferably 8 or 10, carbon atoms, preferably with the proviso, that referring to all alkyl-phosphine oxide of general formula 1 contained in the extracting medium, the molar ratio of all alkyl radicals containing 8 and 10 carbon atoms is in the range of from 1.0:2.0 to 2.0:1.0, preferably from 1.0:1.5 to 1.5:1.0, even more preferably from 1.0:1.2 to 1.2:1.0.

Preferably the method according to the instant invention is characterized in, that in the extracting medium the at least one alkyl-phosphine oxide accounts for at least 50 wt.-%, preferably at least 80 wt.-%, even more preferably at least 90 wt.-%, the most preferably at least 97 wt.-%, of the total extracting medium.

In a preferred method according to the instant invention the extracting medium further contains at least one alkane comprising at least 12 carbon atoms, preferably 12 to 18 carbon atoms, even more preferably selected from the group consisting of tetradecane, pentadecane, hexadecane, heptadecane and octadecane. In a further preferred method according to the instant invention the extracting medium may comprise a mixture of alkanes. In another example, the alkane may be a branched alkane.

In a preferred method according to the instant invention the extracting medium contains aside the phosphine oxide a second organic component. The second organic component contains at least 12 carbons. The second organic component is an alkane linear or branched that may be selected from the group consisting, tetradecane, pentadecane, hexadecane, heptadecane, and octadecane or mixtures of alkanes such as white mineral oil (Fragoltherm-Q-32-N). Furthermore the second organic component may comprise of an aromatic hydrocarbon that may be selected from the group consisting of, diisopropylbiphenyl, partly hydrogenated terphenyl, dibenzyltoluol and diisopropylnaphthalene or a mix of aromatic solvents such as Solvesso 200. Another possibility is to use an alcohol that may be selected from the group consisting of, oleyl alcohol, 2-octyldodecanol and 2-hexyldodecanol as the second organic component.

The weight ratio of the alkyl-phosphine oxide to alkane in the extracting medium according to any aspect of the present invention preferably is between 1:100 to 100:1. Even more in particular, the weight ratio of the alkyl-phosphine oxide to alkane may be selected within the range of from 1:2 to 50:1, more preferably from 1:1 to 97:3. In the example, the alkane may be hexadecane and therefore the weight ratio of the alkyl-phosphine oxide to hexadecane may be about 97:3. The term ‘about’ as used herein refers to a variation within 20 percent. In particular, the term “about” as used herein refers to +/−20%, more in particular, +/−10%, even more in particular, +/− 5% of a given measurement or value.

The extracting medium according to any aspect of the present invention may efficiently extract the organic acid and/or alcohol (i.e. carbonic acid, aliphatic acid, aliphatic acid ester and aliphatic alcohol) into the extracting medium. This extracting medium of is a mixture of at least one alkylphosphine oxide containing at least two different alkyl radicals per alkyl-phosphine oxide molecule, and at least one alkane may be considered suitable in the method according to any aspect of the present invention as the mixture works efficiently in extracting the desired organic acid and/or alcohol in the presence of the aqueous production medium. The alkane may be a straight or a branched alkane.

In another example, the extracting medium of a mixture of at least one alkyl-phosphine oxide containing at least two different alkyl radicals per alkyl-phosphine oxide molecule and at least one partially hydrogenated aromatic hydrocarbon may be considered suitable in the method according to any aspect of the present invention as the mixture works efficiently in extracting the desired organic acid and/or alcohol in the presence of the aqueous production medium. In particular, the mixture of at least one alkyl-phosphine oxide containing at least two different alkyl radicals per alkyl-phosphine oxide molecule and at least one partially hydrogenated aromatic hydrocarbon may be considered to work better than any method currently known in the art for extraction organic acid and/or alcohol as it does not require any special equipment to be carried out and it is relatively easy to perform with a high product yield. Further, the extracting medium according to any aspect of the present invention in combination with alkane or partially hydrogenated aromatic solvent is also not toxic for microorganisms.

Preferably the method according to the instant invention is characterized in, that the aqueous medium in (a) contains a microorganism, preferably a living microorganism, producing the carbonic acid, aliphatic acid, aliphatic acid ester and/or aliphatic alcohol.

The microorganisms producing the carbonic acid, aliphatic acid, aliphatic acid ester and/or aliphatic alcohol according to any aspect of the present invention may be cultivated with any culture media, substrates, conditions, and processes generally known in the art for culturing microorganisms. This allows for the carbonic acid, aliphatic acid, aliphatic acid ester and/or aliphatic alcohol to be produced using a biotechnological method. Depending on the microorganism that is used for carbonic acid, aliphatic acid, aliphatic acid ester and/or aliphatic alcohol production, appropriate growth medium, pH, temperature, agitation rate, inoculum level, and/or aerobic, microaerobic, or anaerobic conditions are varied. A skilled person would understand the other conditions necessary to carry out the method according to any aspect of the present invention. In particular, the conditions in the container of the microorganisms (e.g. fermenter) may be varied depending on the microorganisms used. The varying of the conditions to be suitable for the optimal functioning of the microorganisms is within the knowledge of a skilled person.

Preferably the method according to the instant invention is characterized in, that the pH of the aqueous medium during step a) is from 5.0 to 9.0, preferably from 5.8 to 8.0, and particularly preferably from 6.5 to 7.5. The “pH” in connection with the present invention is defined as the value which is measured for the relevant composition at 25° C. after stirring for 5 minutes using a calibrated pH electrode in accordance with ISO 4319 (1977).

The pressure may be between 1 and 10 bar. The microorganisms may be cultured at a temperature ranging from about 20° C. to about 80° C. In one example, the microorganism may be cultured at 37° C.

In some examples, for the growth of the microorganism and for its production of the carbonic acid, aliphatic acid, aliphatic acid ester and/or aliphatic alcohol, the aqueous medium may comprise any nutrients, ingredients, and/or supplements suitable for growing the microorganism or for promoting the production of the carbonic acid, aliphatic acid, aliphatic acid ester and/or aliphatic alcohol. In particular, the aqueous medium may comprise at least one of the following: carbon sources, nitrogen sources, such as an ammonium salt, yeast extract, or peptone; minerals; salts; cofactors; buffering agents; vitamins; and any other components and/or extracts that may promote the growth of the microorganism. The culture medium to be used must be suitable for the requirements of the particular strains. Descriptions of culture media for various microorganisms are given in “Manual of Methods for General Bacteriology”.

The term “an aqueous solution” or “medium” comprises any solution comprising water, mainly water as solvent that may be used to keep the microorganism according to any aspect of the present invention, at least temporarily, in a metabolically active and/or viable state and comprises, if such is necessary, any additional substrates. The person skilled in the art is familiar with the preparation of numerous aqueous solutions, usually referred to as media that may be used to keep and/or culture the cells, for example LB medium in the case of *E. coli*, ATCC1754-Medium may be used in the case of *C. ljungdahii*. It is advantageous to use as an aqueous solution a minimal medium, i.e. a medium of reasonably simple composition that comprises only the minimal set of salts and nutrients indispensable for keeping the cell in a metabolically active and/or viable state, by contrast to complex mediums, to avoid dispensable contamination of the products with unwanted side products. For example, M9 medium may be used as a minimal medium. The cells are incubated with the carbon source sufficiently long enough to produce the desired product. For example for at least 1, 2, 4, 5, 10 or 20 hours. The temperature chosen must be such that the cells according to any aspect of the present invention remains catalytically competent and/or metabolically active, for example 10 to 42° C., preferably 30 to 40° C., in particular, 32 to 38° C. The aqueous medium according to any aspect of the present invention also includes the medium in which the carbonic acid, aliphatic acid, aliphatic acid ester and/or aliphatic alcohol is produced. It mainly refers to a medium where the solution comprises substantially water. In one example, the aqueous medium in which the cells are used to produce the carbonic acid, aliphatic acid, aliphatic acid ester and/or aliphatic alcohol is the very medium which contacts the extraction medium for extraction of the carbonic acid, aliphatic acid, aliphatic acid ester and/or aliphatic alcohol.

A preferred method according to the instant invention is characterized in, that the carbonic acid in total is contained in an amount of from 0,00001 wt.-% to 0.00100 wt.-%, preferably from 0,00005 wt.-% to 0,00050 wt.-%, more preferably from 0,00008 wt.-% to 0,00012 wt.-%, in the aqueous medium, with the weight percent referring to the total aqueous medium.

A preferred method according to the instant invention is characterized in, that the aliphatic acid, aliphatic acid ester and/or aliphatic alcohol, when containing two carbon atoms, in total is contained in an amount of from 0,0001 wt.-% to 0.0100 wt.-%, preferably from 0,0005 wt.-% to 0.0050 wt.-%, more preferably from 0,0008 wt.-% to 0.0012 wt.-%, in the aqueous medium, with the weight percent referring to the total aqueous medium.

A preferred method according to the instant invention is characterized in, that the aliphatic acid, aliphatic acid ester and/or aliphatic alcohol, when containing three or four carbon atoms, in total is contained in an amount of from 0.01 wt.-% to 1.00 wt.-%, preferably from 0.05 wt.-% to 0.50 wt.-%, more preferably from 0.08 wt.-% to 0.12 wt.-%, in the aqueous medium, with the weight percent referring to the total aqueous medium.

A preferred method according to the instant invention is characterized in, that the aliphatic acid, aliphatic acid ester and/or aliphatic alcohol, when containing five or six carbon atoms, in total is contained in an amount of from 0.1 wt.-% to 10.00 wt.-%, preferably from 0.5 wt.-% to 5.0 wt.-%, more preferably from 0.8 wt.-% to 1.2 wt.-%, in the aqueous medium, with the weight percent referring to the total aqueous medium.

A further aspect of the instant invention is an alkyl-phosphine oxide of general formula 1 general formula 1

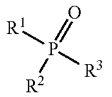

with $R^1$, $R^2$ and $R^3$ selected from alkyl radicals containing 6 to 12, preferably 8 to 10, more preferably 8 or 10, carbon atoms, with the proviso, that at least two of $R^1$, $R^2$ and $R^3$ differ from each other, preferably with the proviso, that the molar ratio of all alkyl radicals containing 8 or 10 carbon atoms is in the range of from 1.0:2.0 to 2.0:1.0, preferably from 1.0:1.5 to 1.5:1.0, even more preferably from 1.0:1.2 to 1.2:1.0.

Yet another further aspect of the instant invention is the use of at least one alkyl-phosphine oxide, that contains at least two different alkyl radicals per alkyl-phosphine oxide molecule, for extracting at least one selected from carbonic acid, aliphatic acid, aliphatic acid ester and aliphatic alcohol from an aqueous medium.

The inventive use preferably uses the alkyl-phosphine oxide preferably in the same preferred ways as used in the method of the instant invention and, of course, preferably is used for the same preferred aliphatic acids, aliphatic acids ester and aliphatic alcohols as described above.

The foregoing describes preferred embodiments, which, as will be understood by those skilled in the art, may be subject to variations or modifications in design, construction or operation without departing from the scope of the claims. These variations, for instance, are intended to be covered by the scope of the claims.

EXAMPLES

Toxicity Tests:

Example 1

General Description of the Tests:

To test the toxicity of different trialkylphosphines (TAPO), batch fermentations were mixed with those trialkylphosphines as an additive and the reactivity of the fermenters were monitored. These results were compared with a corresponding positive control run, which is a batch fermentation under standard conditions without any additive. The reactivity of the bacteria was monitored by the formation of carboxylic acids (C4+C6). The concentration of butyric acid and hexanoic acid was analysed by HPLC and 1H-NMR. If the quotient of test run and positive control is in proximity to 100%, the corresponding additive is regarded as non-toxic. If the quotient of test run and positive control is in proximity to 0%, the corresponding additive is regarded as non-toxic. Each run was reproduced at least once. Shown results are average values.

General Description of Standard Fermentation:

The precultivation of *Clostridium kluyveri* was carried out in a 1000 mL pressure-resistant glass bottle in 250 ml of EvoDM24 medium (pH 5.5; 0.429 g/L Mg-acetate, 0.164 g/l Na-acetate, 0.016 g/L Ca-acetate, 2.454 g/l K-acetate, 0.107 mL/L $H_3PO_4$ (8.5%), 0.7 g/L $NH_4$acetate, 0.35 mg/L Co-acetate, 1.245 mg/L Ni-acetate, 20 μg/L d-biotin, 20 μg/L folic acid, 10 μg/L pyridoxine-HCl, 50 μg/L thiamine-HCl, 50 μg/L Riboflavin, 50 μg/L nicotinic acid, 50 μg/L Ca-pantothenate, 50 μg/L Vitamin B12, 50 μg/L p-aminobenzoate, 50 μg/L lipoic acid, 0.702 mg/L $(NH_4)_2Fe(SO_4)_2$×4 $H_2O$, 1 ml/L L-cysteine (93.5 mM), 20 mL/L ethanol, 0.37 g/L acetic acid) at 37° C., 150 rpm and a ventilation rate of 1 L/h with a mixture of 25% $CO_2$ and 75% $N_2$ in an open water bath shake. The gas was discharged into the headspace of the reactor. The pH was hold at 5.5 by automatic addition of 2.5 M $NH_3$ solution. Fresh medium was continuously feeded to the reactor with a dilution rate of 2.0 $d^{-1}$ and fermentation broth continuously removed from the reactor through a KrosFlo® hollow fibre polyethersulfone membrane with a pore size of 0.2 μm (Spectrumlabs, Rancho Dominguez, USA) to retain the cells in the reactor and hold an $OD_{600\ nm}$ of ~1.5.

For the main culture 100 ml of Veri01 medium (pH 6.5; 10 g/L potassium acetate, 0.31 g/L $K_2HPO_4$, 0.23 g/L $KH_2PO_4$, 0.25 g/L $NH_4Cl$, 0.20 g/L $MgSO_4$×7 $H_2O$, 10 μl/L HCl (7.7 M), 1.5 mg/L $FeCl_2$×4 $H_2O$, 36 μg/L $ZnCl_2$, 64 μg/L $MnCl_2$×4 $H_2O$, 6 μg/L $H_3BO_3$, 190 μg/L $CoCl_2$×6 $H_2O$, 1.2 μg/L $CuCl_2$×6 $H_2O$, 24 μg/L $NiCl_2$×6 $H_2O$, 36 μg/L $Na_2MO_4$×2 $H_2O$, 0.5 mg/L NaOH, 3 μg/L $Na_2SeO_3$×5 $H_2O$, 4 μg/L $Na_2WO_4$×2 $H_2O$, 100 μg/L vitamin B12, 80 μg/L p-aminobenzoic acid, 20 μg/L D(+) Biotin, 200 μg/L nicotinic acid, 100 μg/L D-Ca-pantothenate, 300 μg/L pyridoxine hydrochloride, 200 μg/l thiamine-HCl×$2H_2O$, 20 ml/L ethanol, 2.5 g/L $NaHCO_3$, 65 mg/L glycine, 24 mg/L histidine, 64.6 mg/L isoleucine, 93.8 mg/L leucine, 103 mg/L lysine, 60.4 mg/L arginine, 21.64 mg/L L-cysteine-HCl, 21 mg/L methionine, 52 mg/L proline, 56.8 mg/L serine, 59 mg/L threonine, 75.8 mg/L valine, 2.5 mL/L HCL 25%) in a 250 ml bottle were inoculated with centrifuged cells from the preculture to an $OD_{600\ nm}$ of 0.1. The culture was capped with a butyl rubber stopper and incubated at 37° C. and 150 rpm in an open water bath shaker for 47 h under 100% $CO_2$ atmosphere. The cultivation duration was approximately 140 hours.

During cultivation several 5 mL samples were taken to determinate $OD_{600\ nm}$, pH and product formation. The determination of the product concentrations was performed by semiquantitative 1H-NMR spectroscopy. As an internal quantification standard sodium trimethylsilylpropionate (T(M)SP) was used.

If added, the corresponding trialkylphosphine was added briefly after inoculation of the main culture in a ratio of 1 mL trialkylphosphine/100 mL broth volume.

Results:

| entry | Added TAPO type* | Carboxylic acid formation (test run/control) [%] |
|---|---|---|
| 1 | C8 (6% in tetradecane) | 112 |
| 2 | C8/C10 | 119 |

*Carbon number indicates the length of the alkyl chain. If two carbon numbers are shown, the corresponding trialkylphosphine exhibits both chain length in a statistic distribution.

As can be seen by the amount of product formation above, the trialkylphosphine with two different alkyl chains is less harmful to the cells than the pure C8-substituted trialkylphosphine.

Example 2

To test the toxicity of different aromatic hydrocarbons, batch fermentations were mixed with those aromatic hydrocarbons as an additive and the reactivity of the fermenters were monitored. These results were compared with a corresponding positive control run, which is a batch fermentation under standard conditions without any additive. The reactivity of the bacteria was monitored by the formation of carboxylic acids (C4+C6). The concentration of butyric acid and hexanoic acid was analyzed by HPLC. If the quotient of test run and positive control is in proximity to 100%, the corresponding additive is regarded as non-toxic. If the quotient of test run and positive control is in proximity to 0%, the corresponding additive is regarded as toxic.

For the main culture 90 ml of Veri01 medium as described in Example 1 were inoculated with cells from the preculture to an OD600 nm of 0.06. The culture was capped with a butyl rubber stopper and incubated at 37° C. and 150 rpm in an open water bath shaker for 140 h under N2/H2 atmosphere. During cultivation several 5 mL samples were taken to determinate OD600 nm, pH and product formation. The determination of the product concentrations was performed by HPLC analysis. If added, the corresponding aromatic hydrocarbon was added before inoculation of the main culture in a ratio of 1 mL aromatic hydrocarbon/100 mL broth volume.

| Entry | Added solvent | Carboxylic acid formation (test run/control) [%] |
|---|---|---|
| 1 | Fragoltherm 660 (partly hydrogenated terphenyl) | 97 |
| 2 | Fragoltherm HT (dibenzyltoluol) | 97 |

As can be seen by the amount of product formation above, the partly aromatic solvents have little effect on the productivity of the cells.

EXTRACTION EXAMPLES

Example 3

General Description of Extraction of Organic Acids

A mixture of hexanoic acid (10 g/Kg), butyric acid (2.5 g/Kg), acetic acid (0.25 g/Kg) and ethanol (12 g/Kg) in distilled water was neutralized by addition of aqueous ammonia to a pH of 5.8. This aqueous solution was placed in a separation funnel and vigorously mixed with an organic mixture of a trialkylphosphine in alkane or pure trialkylphosphine. The mass ratio of aqueous phase to organic phase was 9 to 1. The extraction of acids into the organic phased caused a strong pH shift upwards in the aqueous phase at concentrations of 50% TAPO and higher. Therefore, the pH was corrected in those samples to 5.8 by the addition of a sufficient amount of aqueous acetic acid. After intense mixing the phases were allowed to separate and individually analysed by HPLC or $^{1}H$-NMR to determine the concentration of the compounds in each phase. The distribution of the compounds is indicated by the distribution constant Kd, whereat Kd is the ratio of the concentration in the organic phase divided by the concentration in the aqueous phase.

| entry | Added TAPO type* | Aq. Carboxylic acid conc. [g/kg] (before/after) | Org. carboxylic acid conc. [g/kg] | Kd** |
|---|---|---|---|---|
| 1 | C8 (6% in tetradecane) | H: 10.18/9.11 | H: 9.67 | 1.06 |
| 2 | C8/C10 (6% in tetradecane) | H: 10.18/8.87 | H: 11.89 | 1.34 |
| 3 | C8/C10 (50% in tetradecane) | H: 10.33/1.70<br>B: 2.38/1.86<br>A: 5.71/5.66 | H: 80.39<br>B: 4.81<br>A: 0.44 | H: 47<br>B: 2.6<br>A: 0.08 |
| 4 | C8/C10 | H: 10.24/0.75<br>B: 2.36/1.37<br>A: 6.91/6.71 | H: 89.49<br>B: 9.30<br>A: 1.85 | H: 119<br>B: 6.8<br>A: 0.28 |

*Carbon number indicates the length of the alkyl chain. If two carbon numbers are shown, the corresponding trialkylphosphine exhibits both chain length in a statistic distribution.
**Kd is the ratio of the concentration in the organic phase divided by the concentration in the aqueous phase.

As can be seen by the table above, the trialkylphosphine with two different alkyl chains gives very much higher Kds than the pure C8-substituted trialkylphosphine.

Example 4

General Description of Extraction of Hexanol

A solution of hexanol (4 g/Kg) in distilled water was prepared. An ammonium acetate buffer (ammonium acetate 0.6 g/Kg adjusted to pH 5.8 by addition of acetic acid) was added to the solution to keep the pH close to 5.8 during extraction. The aqueous solution was placed in a separation funnel and vigorously mixed with an organic mixture of a trialkylphosphine in alkane or pure trialkylphosphine. The mass ratio of aqueous phase to organic phase was 9 to 1. After intense mixing the phases were allowed to separate and individually analysed by HPLC or $^{1}H$-NMR to determine the concentration of hexanol in each phase. The distribution of hexanol is indicated by the distribution constant Kd, whereat Kd is the ratio of the concentration in the organic phase divided by the concentration in the aqueous phase.

Results of Hexanol Extraction with Buffer in Aqueous Phase:

| Entry | Added TAPO type* | Equilibrium pH | Aq. Hexanol conc. [g/Kg] (before/after) | Org. Hexanol conc. [g/kg] | Kd** hexanol |
|---|---|---|---|---|---|
| 1 | none (100% tetradecane) | 5.77 | 4.15/2.75 | 12.44 | 4.5 |
| 2 | C8/C10 (6% in tetradecane) | 5.77 | 4.15/1.40 | 24.42 | 17 |
| 3 | C8/C10 | 5.77 | 4.15/0.19 | 36.33 | 190 |

*Carbon number indicates the length of the alkyl chain. If two carbon numbers are shown, the corresponding trialkylphosphine exhibits both chain length in a statistic distribution.
**Kd is the ratio of the concentration in the organic phase divided by the concentration in the aqueous phase.

Results of Hexanol Extraction without Buffer in Aqueous Phase:

| Entry | Added TAPO type* | Equilibrium pH | Aq. Hexanoic acid conc. [g/Kg] (before/after) | Org. Hexanol conc. [g/kg] | Kd** hexanol |
|---|---|---|---|---|---|
| 1 | none (100% tetradecane) | 7.01 | 3.70/2.40 | 11.65 | 4.9 |
| 2 | C8/C10 (6% in tetradecane) | 6.83 | 3.70/1.25 | 22.47 | 18 |
| 3 | C8/C10 | 8.23 | 3.70/0.17 | 30.48 | 180 |

*Carbon number indicates the length of the alkyl chain. If two carbon numbers are shown, the corresponding trialkylphosphine exhibits both chain length in a statistic distribution.
**Kd is the ratio of the concentration in the organic phase divided by the concentration in the aqueous phase.

As can be seen by the tables above, the trialkylphosphine with two different alkyl chains can be applied over a broad pH range.

Example 5

General Description of Extraction of Organic Acids A mixture of hexanoic acid (5 g/kg), butyric acid (2.84 g/kg), acetic acid (1.34 g/kg) and ethanol (2.77 g/kg) in distilled water was neutralized by addition of aqueous ammonia to a pH of 5.8. This aqueous solution was placed in a separation funnel and vigorously mixed with an organic mixture of a trialkylphosphine in fragoltherm 660. The mass ratio of aqueous phase to organic phase was 9 to 1. The extraction of acids into the organic phased caused a strong pH shift upwards in the aqueous phase. Therefore, the pH was corrected in those samples to 5.8 by the addition of a sufficient amount of hexanoic acid. After intense mixing the phases were allowed to separate and individually analyzed by HPLC to determine the concentration of the compounds in each phase. The distribution of the compounds is indicated by the distribution constant Kd, whereat Kd is the ratio of the concentration in the organic phase divided by the concentration in the aqueous phase.

| entry | extractant* | Aq. carboxylic acid conc. [g/kg] | Org. carboxylic acid conc. [g/kg] | Kd** |
|---|---|---|---|---|
| 1 | C8/C10 (50% in fragoltherm 660) | H: 6.00 g/kg<br>B: 2.39 g/kg<br>A: 2.74 g/kg | H: 119 g/kg<br>B: 4.1 g/kg<br>A: 0 g/kg | H: 20<br>B: 1.7<br>A: 0 |

*Carbon number indicates the length of the alkyl chain. If two carbon numbers are shown, the corresponding trialkylphosphine exhibits both chain length in a statistic distribution
**Kd is the ration of the concentration in the organic phase divided by the concentration in the aqueous phase.

As can be seen in the table above, the Kd values using partly aromatic solvent is not affected.

The invention claimed is:

1. A method of extracting at least one compound selected from the group consisting of: carbonic acid, an aliphatic acid, an aliphatic acid ester, and an aliphatic alcohol from an aqueous medium, the method comprising the steps:

(a) contacting the carbonic acid, aliphatic acid, aliphatic acid ester or aliphatic alcohol in the aqueous medium comprising living microorganisms with an extracting medium comprising at least one alkyl-phosphine oxide and a second organic component with at least 12 carbons wherein said second organic component is a linear or branched alkane, an aromatic hydrocarbon, or an alcohol, for a time sufficient to extract the carbonic acid, aliphatic acid, aliphatic acid ester or aliphatic alcohol from the aqueous medium into the extracting medium; and (b) separating the extracting medium with the extracted carbonic acid, aliphatic acid, aliphatic acid ester or aliphatic alcohol from the aqueous medium;

wherein:

the at least one alkyl-phosphine oxide comprises at least two different straight or branched alkyl radicals per alkyl-phosphine oxide molecule;

the aqueous medium in step (a) comprises a living microorganism producing the carbonic acid, aliphatic acid, aliphatic acid ester or aliphatic alcohol, and the living microorganism is contacted by the extracting medium during extraction;

the at least one alkyl-phosphine oxide accounts for at least 50 wt.-% of the total extracting medium and the amount of carbonic acid, aliphatic acid, aliphatic acid ester or aliphatic alcohol formed in the presence of the alkyl-phosphine oxide is not reduced compared to when said alkyl-phosphine oxide is absent;

the pH of the aqueous medium during step (a) is from 5.0 to 9.0; and the microorganism is cultured at a temperature ranging from about 20° C. to about 80° C.

2. The method of claim 1, wherein:

the aliphatic acid is a monofunctional aliphatic acid;

in the aliphatic acid ester, the aliphatic acid radical is a monofunctional aliphatic acid radical; and the aliphatic alcohol is a monohydric alcohol.

3. The method of claim 2, wherein alkanoic chains in the aliphatic acid, the aliphatic acid ester, and the aliphatic alcohol are unbranched.

4. The method of claim 1, wherein the aliphatic acid, aliphatic acid ester and/or aliphatic alcohol comprises 4 to 18 carbon atoms.

5. The method of claim 4, wherein the aliphatic acid, aliphatic acid ester and/or aliphatic alcohol comprises 6 to 8 carbon atoms.

6. The method of claim 4, wherein the aliphatic acid, aliphatic acid ester and/or aliphatic alcohol is selected from the group consisting of: butanol, pentanol, hexanol, butanoic acid, pentanoic acid, hexanoic acid, and the methyl- and ethyl-esters of butanoic acid, pentanoic acid, and hexanoic acid.

7. The method of claim 1, wherein the alkyl-phosphine oxide is an alkyl-phosphine oxide of general formula 1:

general formula 1

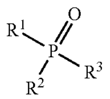

wherein $R^1$, $R^2$ and $R^3$ are straight or branched alkyl radicals comprising 4 to 18 carbon atoms; with the proviso, that at least two of $R^1$, $R^2$ and $R^3$ differ from each other.

8. The method of claim 7, wherein $R^1$, $R^2$ and $R^3$ are straight or branched alkyl radicals comprising 6 to 12 carbon atoms.

9. The method of claim 7, wherein $R^1$, $R^2$ and $R^3$ are straight or branched alkyl radicals comprising 8 to 10 carbon atoms.

10. The method of claim 9, wherein, relative to all alkyl-phosphine oxides of general formula 1 in the extracting medium, the molar ratio of all alkyl radicals of the alkyl-phosphine oxides comprising 8 and 10 carbon atoms is in the range of from 1.0:2.0 to 2.0:1.0.

11. The method of claim 10, wherein the molar ratio of all alkyl radicals of the alkyl-phosphine oxides comprising 8 and 10 carbon atoms is in the range of from 1.0:1.2 to 1.2:1.0.

12. The method of claim 1, wherein the at least one alkyl-phosphine oxide accounts for at least 80 wt.-% of the total extracting medium.

13. The method of claim 1, wherein the at least one alkyl-phosphine oxide accounts for at least 90 wt.-% of the total extracting medium.

14. The method of claim 1, wherein the extracting medium further comprises at least one alkane comprising at least 12 carbon atoms.

15. The method of claim 1, wherein the extracting medium further comprises at least one alkane comprising 12 to 18 carbon atoms.

16. The method of claim 15, wherein the weight ratio of alkyl-phosphine oxide to alkane in the extracting medium is between 1:2 and 50:1.

17. The method of claim 1, wherein the extracting medium comprises an aromatic solvent.

18. The method of claim 15, wherein the second organic component with at least 12 carbons is selected from the group consisting of: tetradecane, pentadecane, hexadecane, heptadecane, octadecane, diisopropylbiphenyl, partly hydrogenated terphenyl, dibenzyltoluol, diisopropylnaphthalene, oleyl alcohol, 2-octyldodecanol, 2-hexyldodecanol and combinations thereof.

19. The method of claim 1, wherein the extracting medium is present when the carbonic acid, aliphatic acid, aliphatic acid ester or aliphatic alcohol is biotechnologically produced.

* * * * *